(12) United States Patent
Haas et al.

(10) Patent No.: US 6,846,306 B1
(45) Date of Patent: Jan. 25, 2005

(54) SINGLE CELL ELECTROPORATION

(75) Inventors: Kurt Haas, Goshen, NY (US); Wun Chey Sin, Huntington, NY (US); Ashkan Javaherian, Huntington, NY (US); Zheng Li, Huntington, NY (US); Hollis Cline, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/685,310

(22) Filed: Oct. 10, 2000

(51) Int. Cl.[7] .......................... A61M 31/00; A61N 1/30; C12M 1/42; C12M 3/00
(52) U.S. Cl. .......................... 604/522; 604/20; 435/461; 435/285.2
(58) Field of Search .......................... 604/19, 20–22, 604/500–502, 506, 512, 181, 522; 607/59, 2; 600/372, 373, 377, 378, 381; 606/32, 41, 42, 43, 44, 45, 48; 435/461, 285.1, 285.2

(56) References Cited

U.S. PATENT DOCUMENTS

| | | | | |
|---|---|---|---|---|
| 5,007,995 A | * | 4/1991 | Takahashi et al. | 435/285.2 |
| 5,789,213 A | * | 8/1998 | Hui et al. | 435/461 |
| 5,911,223 A | * | 6/1999 | Weaver et al. | 128/898 |
| 5,993,434 A | * | 11/1999 | Dev et al. | 604/20 |
| 6,233,482 B1 | * | 5/2001 | Hofmann et al. | 604/21 |
| 6,245,564 B1 | * | 6/2001 | Goldman et al. | 435/368 |
| 6,352,535 B1 | * | 3/2002 | Lewis et al. | 606/45 |
| 6,520,950 B1 | * | 2/2003 | Hofmann et al. | 604/503 |
| 6,521,430 B1 | * | 2/2003 | Orwar et al. | 435/173.6 |

OTHER PUBLICATIONS

Li, et al., Nature Neurosci 3, 217–225 (2000).
Nedivi, et al., Science 281, 1863–1866 (1998).
Wu G–Y and Cline HT, Science 279, 222–226 (1998).
Zou D–J and Cline HT, Neuron 16; 529–539 (1996).
Davis, et al., Neuron 19, 561–73 (1997).
Hayashi, et al., Science 287, 2262–2267 (2000).
Neumann, et al., Bioelectrochem Bioenerg 48, 3–16 (1999).
Ho, et al., Crit Rev Biotechnol 16, 349–62 (1996).
Sakamoto, et al., FEBS Lett 426, 337–41 (1998).
Koshiba–Takeuchi, et al. Science 287, 134–7 (2000).
Akamatsu, et al., Proc Natl Acad Sci U S A 96, 9885–90 (1999).
Miyasaka, et al., NeuroReport 10, 2319–23 (1999).
Muramatsu, et al., Biochem Biophys Res Commun 230, 376–80 (1997).
Neumann, et al., Biophysical J., 74, 98–108 (1998).
Zito, et al., Neuron 22, 719–729 (1999).
Atkins, et al., Biotechniques 27, 94–100 (1999).
Neumann, et al., Biophysical J. 71, 868–877 (1996).
Teruel, et al., J Neurosci Methods, 93, 37–48 (1999).
Matz, et al., Nat Biotechnol 17, 969–73 (1999).

\* cited by examiner

Primary Examiner—Nicholas D. Lucchesi
Assistant Examiner—Mark K. Han
(74) Attorney, Agent, or Firm—Dilworth & Barrese, LLP

(57) ABSTRACT

A single cell electroporation assembly and method involve delivery of a substance into a single cell. The substance is combined into an electroporation fluid and placed into a container having a distal opening. The distal opening of the container is placed in proximity to a target cell. Electrical pulses are delivered between a first electrode which is at least partially disposed in the container, and a second electrode outside the cell, the cell being positioned between the distal opening and the second electrode. The electrical pulses induce temporary formation of pores in the cell membrane and the substance enters the cell through the pores by passive diffusion or by active electrophoretic motion.

21 Claims, 6 Drawing Sheets

A (Green)     B (Red)     C (Yellow)

SINGLE CELL ELECTROPORATION

GOVERNMENT RIGHTS

This invention was funded, at least in part, under grants from the National Eye Institute of the National Institutes of Health, Nos. EY11261 and EY06922-03. The Government may therefore have certain rights in the invention.

BACKGROUND

Recent large-scale genetic screens have uncovered a multitude of genes implicated in brain development, learning and memory, regeneration, and neurological diseases. Determining the function of these genes in vivo necessitates advanced techniques for controlling the timing and location of gene expression, combined with specific assays of brain cell function or morphology. In some cases it will be important to introduce genes into postmitotic cells which are refractory to most available gene transfer methods. In other cases, introduction of genes of interest into pluripotent cells such as stem cells will be required to determine their function or to provide therapeutic value.

Morphologic studies of neuronal development in *Xenopus* following viral gene transfer and in transgenic *Drosophila* exemplify the potential for elucidating gene function when the genetic makeup of individual neurons can be manipulated and the consequences of the gene transfer on neuronal structure can be observed by in vivo imaging techniques (Li, et al., Nature Neurosci 3, 217–225 (2000), Nedivi, et al., Science 281, 1863–1866 (1998), Wu G-Y and Cline H T, Science 279, 222–226 (1998); Zou D-J and Cline H T, Neuron 16; 529–539 (1996), Davis, et al., Neuron 19, 561–73 (1997)). As another example, side-by-side comparison of the synaptic properties of individual genetically modified neurons with unaffected neurons in the same brain provides a powerful tool for the elucidation of gene function (Hayashi, et al., Science 287, 2262–2267 (2000). However, current techniques for spatially and temporally controlled introduction of genes of interest into single cells within central nervous system tissue is limited. One versatile technique applicable to this problem is electroporation.

Electroporation is a popular technique for introducing macromolecules, including DNA, RNA, dyes, proteins and various chemical agents, into cells. Electroporation refers to the permeabilization of cell membranes by application of short duration electric field pulses, traditionally between relatively large plate electrodes (Neumann, et al., Bioelectrochem Bioenerg 48, 3–16 (1999); Ho, et al., Crit Rev Biotechnol 16, 349–62 (1996)). Large external electric fields induce high transmembrane potentials leading to the formation of minute pores (20–120 nm diameter) restricted to small regions of the cell membrane (<0.1%) adjacent to the electrodes. During the electric pulse, charged macromolecules, including DNA, are actively transported by electrophoresis across the cell membrane through these pores (Neumann, et al., Biophys J 71, 868–77 (1996)). Noncharged molecules can also enter through the pores by passive diffusion. Upon pulse termination, pores reseal over hundreds of milliseconds as measured by recovery of normal membrane conductance values (Ho, 1996, supra).

Although electroporation is an established method for implantation of exogenous materials in various cell types including both prokaryotic and eukaryotic cells, e.g., transformation and transfection of cell types ranging from bacteria to mammalian cell lines, its application to brain cells such as neurons and glial cells in intact tissues has been relatively limited. Electroporation has been successful for gene transfer into large numbers of neurons in chick (Atkins, et al., Biotechniques 28, 94–6, 98, 100 (2000); Sakamoto, et al., FEBS Lett 426, 337–41 (1998); Koshiba-Takeuchi, et al. Science 287, 134–1 (2000)) and mouse embryos (Akamatsu, et al., Proc Natl Acad Sci USA 96, 9885–90 (1999); Miyasaka, et al., Neuroreport 10, 2319–23 (1999)). Electroporation is being utilized for neuronal gene transfer since it has many advantages over more common transfection methods including viral gene transfer, gene gun biolistics, lipofection and microinjection. Electroporation lacks the potentially toxic effects of viruses and lipofection and the potential physical damage due to the biolistic gene gun and microinjection. Electroporation is also significantly more efficient than either lipofection, microinjection or gene gun biolistics, in terms of numbers of transfected cells and the intensity of foreign gene expression (See Muramatsu, et al., Biochem Biophys Res Commun 230, 376–80 (1997)). Few viruses are available which can infect postmitotic brain cells. Viruses are also limited by the size of the foreign DNA that can be inserted into their genome and thereby transferred to cells. This limits the use of viral gene transfer to study the function of large genes and the use of dicistronic complexes to introduce multiple genes into cells. Finally, lipofection can only be used in proliferating cells and results in transient expression lasting only a few days.

In situations where single-cell gene transfer in intact tissues is desired to express multiple genes, current transfection techniques are insufficient. For many applications, co-expression of multiple genes is desired to allow one to visually identify the transfected cells or to study the interaction of multiple proteins. Co-expression of multiple genes may also be required for assays of brain cell structure following expression of a fluorescent protein along with a gene of interest. Low titre virus can be used to sparsely infect cells, but viral infection is subject to the limitations mentioned above. Although gene-gun biolistics may be utilized to deliver multiple genes, it cannot be used in vivo and is thus limited in its application. Gene transfer by microinjection typically requires that DNA be delivered into the cell nucleus. This method is only applicable to cells plated on a coverslip in which a micropipette can be visualized as it penetrates the nucleus using expensive microscopy equipment. While electroporation is a promising transfection technique, precise targeting is not feasible using traditional, large electrodes. However, one of the powerful attributes of electroporation is the ability to localize transfection by controlling exposure to either DNA or the electric field.

SUMMARY OF THE INVENTION

An electroporation assembly is provided which includes a container having a distal opening, the container configured to receive a conductive fluid including a substance for delivery into a cell; a first electrode having at least a portion configured to be disposed within the container and in direct electrical communication with the conductive fluid; and a second electrode positioned in proximity to the distal opening for creating an electric field between the electrodes.

Also provided is a method for delivering a substance into a cell which includes providing a container having a distal opening; placing a conductive fluid including a substance in the container; placing the distal opening in proximity to the cell; and causing an electrical signal to pass through the conductive fluid and the cell wherein the substance passes through the distal opening and enters the cell.

DESCRIPTION OF THE INVENTION

Figure 1:
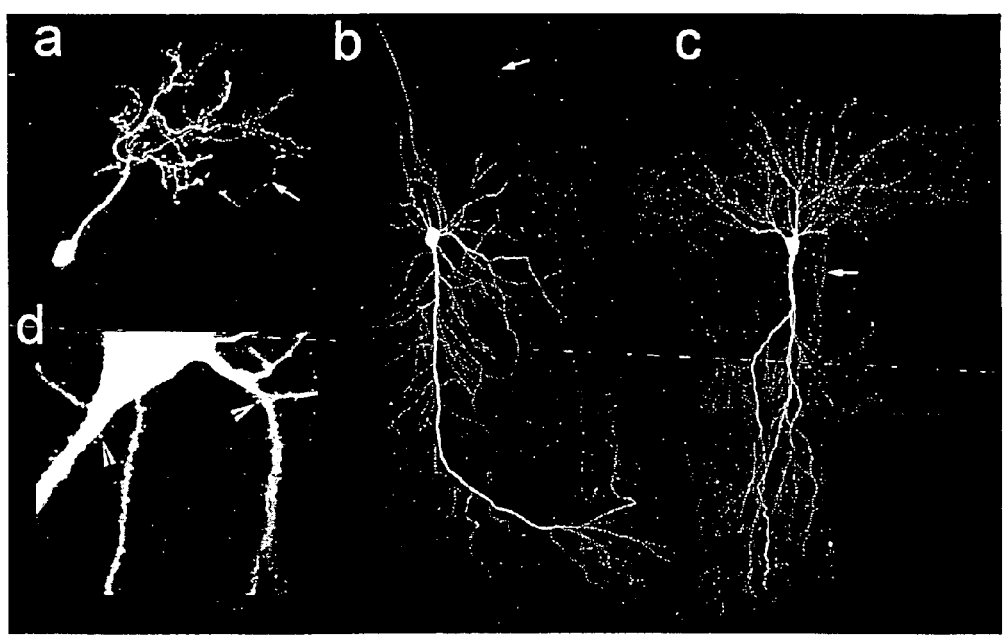
FIG. 1*a* depicts confocal imaging of a single GFP-filled neuron in the tadpole optic tectum. Arrows point to GFP-filled axons.
FIG. 1b depicts confocal imaging of a single GFP-filled neuron in a rat hippocampal CA1 pyramidal cell. Arrows point to GFP-filled axons.
FIG. 1c depicts confocal imaging of a single GFP-filled neuron in a rat hippocampal CA3 pyramidal cell. Arrows point to GFP-filled axons.
FIG. 1d depicts confocal imaging at a higher magnification of the basal dendrites of the CA1 pyramidal cell shown in FIG. 1b which shows filling of dendritic spines (arrowheads).

A novel technique is provided herein for insertion of foreign or exogenous substances into individual cells. This technique is particularly well-suited for use on cells within living organisms, e.g., neurons and brain cells including glial cells such as astrocytes, and other cell types, including stem cells, epithelial cell types and muscle cells. In this technique, for example, if the foreign substance is a gene and the target cell is a brain cell, a container having a distal opening, e.g., a glass pipette, containing DNA solution is inserted into the brain of an anesthetized animal with the tip next to the target cell. Electrical pulses from within the pipette cause DNA to move across the cell membrane into the cell interior. The cell then uses this newly acquired DNA to produce the specific proteins encoded by the DNA. In this manner, the role of cells and particular proteins in brain function can be studied at the single-cell level. In one example of the present invention described in more detail below, a detectable label, e.g., green fluorescent protein was expressed in brain cells of tadpoles and rats, which allowed observation of individual cells growing within the brain over many days.

The present invention is an advancement over current electroporation techniques because it allows exquisite control over the location and number of cells receiving a desired exogenous substance; it can be used at the surface of a single exposed cell or deep within tissue; it can be used in whole live organisms; it is relatively inexpensive and simple; it allows co-transfer of a plurality of materials, e.g., multiple genes, simultaneously; and it lacks many of the toxic side-effects associated with other commonly used gene transfer methods. Most techniques currently available transfer a target substance to a variable number of cells. Single-cell electroporation according to the present invention allows insertion of materials such as genes which provide associated expression of proteins in one cell of a chosen location in an organism while all of the cell's neighbors remain unaffected. Therefore, induced cellular changes are directly due to the foreign DNA introduced in that cell and not to interactions with altered surrounding tissue.

Thus, according to the present invention, molecules to be transferred into a single cell are suspended in a conductive fluid and put into a container having a distal opening such as a syringe, buret or a hollow micropipette, preferably a pulled glass pipette with a sharp tip. In the case of charged molecules such as DNA, the molecule can act as the charge carrier of the conductive solution. The distal opening of the container, preferably having a diameter smaller than the cell diameter, is placed in proximity to and more preferably against the membrane of a target cell. Target cells can be electroporated in culture, in acute tissue preparations, or in the intact organism. Electrical pulses are delivered between an electrode, e.g., a metal wire in the conductive solution in the container and an external ground, such as a metal wire in solution outside of the cell. Electrical pulses induce the temporary formation of pores in the cell membrane. The molecules of interest can then enter the cell through these pores by passive diffusion, or active electrophoretic motion induced by the electric field if the molecules are charged. The container, cell tissue and/or organism may then be removed. Single cell electroporation according to the present invention utilizes the properties of electroporation commonly used to transfer DNA into large numbers of cells using electric fields between relatively large flat plate electrodes. The use of a container having a distal opening such as a micropipette localizes both exposure to the molecule of interest and the electric field, thereby allowing targeting of electroporation of individual cells.

Electrodes used in accordance with the present invention are conductors which establish electrical contact with a non-metallic portion of a circuit. As such, the electrode is an element that is conductive to electron flow and can be made from conductive materials such as silver, platinum, gold, aluminum, stainless steel, titanium, copper, carbon, alloys of the aforementioned materials and the like. Such materials and alloys are well known in the art. Preferably, the electrodes should be made of a relatively non-toxic material. The shape of the electrode is not deemed to be of critical importance as long as at least a portion thereof is configured to fit in the container having the distal opening. Thus, the electrode may be a simple wire, a strip, a sheet or any other suitable shape.

The container having a distal opening is preferably configured to optimize access to the target cell and, as such, preferably has a streamlined shape at least in the area of the distal opening. The container should be made of an insulating material such as glass or other suitable insulating material known to those skilled in the art. The container is configured to receive at least a portion of the electrode and to hold a conductive fluid containing the substance to be inserted into the target cell. For example, the container can include a second opening (other than the distal opening) which is configured to allow the electrode to enter the interior of the container. As mentioned above, a pulled glass pipette with a sharp tip is particularly preferred. The container may optionally include a support to stabilize the electrode and a removable seal to prevent undesired loss of conductive fluid through the second opening. For example, a one-hole rubber stopper can be utilized to seal the electrode and second opening simultaneously.

The distance between a first electrode in the container and a second electrode may vary as long as a sufficient electrical field is created to open pores in a target cell membrane. The first electrode in the container should have a higher potential than the second electrode which, as mentioned above, may be a ground. The electrodes should be able to accommodate a wide range of voltages since the field strength may be varied by routine experimentation depending on the inherent resistance of the circuit which is contributed to by the type of cell, the thickness of the tissue undergoing electroporation, the contents of the conductive fluid, the distance between the electrodes and the nature of the substance being implanted into the cell. The distance between the distal opening of the container and the second electrode should be wide enough to accommodate a single cell, tissue sample, or a living organism. It is contemplated that a tissue or cell support made of a relatively conductive material can be interposed between the distal opening and the second electrode. Alternatively, the cell of the sample can be supported by the second electrode itself, e.g., a ground plate. In another embodiment, the tissue sample can be stretched across the locus of the distal opening and in this manner be located between the first and second electrodes.

Electroporation solutions (also referred to herein as conductive fluids) are well-known in the art. Accordingly, those skilled in the art can fabricate or select conductive fluids for use in accordance with the present invention. In certain embodiments, it is contemplated that charged molecules, e.g., DNA, which are intended to be inserted into a target cell may constitute all or a portion of the charged moiety of the conductive fluid. Any suitable substance may be introduced into a target cell according to the present invention including DNA, RNA, proteins, peptides, metals, dyes, pharmaceutical compounds having therapeutic or physiological activity such as drugs, hormones, growth factors, enzymes, vitamins, minerals and the like. Oligonucleotides, chimeric genes, fusion proteins, ligands, receptors, molecular labeling systems such as fluorescent molecules, radiolabels, antibodies, antigens, avidin, streptavidin, biocytin, and biotin are examples of substances which are suitable for electroporation. Examples of fluorescent molecules (fluorochromes), include green fluorescence protein (GFP), color shifted mutants of GFP including red shifted mutants, yellow shifted mutants and blue shifted mutants, amino coumarin acetic acid (AMCA), fluorscein isothiocyanate (FITC), tetramethylchodamine isothiocyanate (TRITC), Texas Red, Cy3.0, Cy5.0 and dextran conjugates of fluorochromes. Such labels may be used independently or coupled to other molecules such as antibodies, antigens, avidin, streptavidin, and nucleic acid probes. If a particular nucleic acid sequence is the substance to be electroporated into a cell, it may be contained in any suitable vector known in the art. For example, plasmids, cosmids, yeast artificial chromosomes, bacterial artificial chromosomes and the like are all suitable.

Target cells may be electroporated with a variety of electrical pulses. Power sources such as periodic pulse generators are well known in the art and can produce voltage gradients ranging, e.g., from less than about 10 volts/cm to over about 10,000 volts/cm. Square waves can also be generated from pulse generators which produce voltages ranging, e.g., from less than about 10 volts to over about 5,000 volts. Pulse widths may range, e.g., from less than about 0.1 milliseconds (ms) to over about 100 ms. Those with skill in the art can optimize electroporation efficiency for particular substances and target cells by varying the number of electrical pulses delivered, voltage amplitude, pulse shape, and content of the conductive fluid.

Thus, applications for electroporation in accordance with the present invention include: 1) Transfer of DNA or RNA into individual cells for the purpose of controlling protein expression. Both sense sequences for new protein expression, and anti-sense sequences to reduce endogenous protein expression can be introduced; 2) Transfer of DNA into germ cells for the incorporation into chromosomal DNA for the creation of transgenic organisms; 3) Introduction of non-genetic molecules into cells. Both charged and non-charged molecules, including proteins; antibodies, metals, dyes and drugs, can be transferred into individual cells by this technique; and 4) Introduction of DNA and other molecules into stem cells for induction of differentiation, expression of specific proteins, generation of reengineered progenitor cells through insertion of DNA into chromosomes, and to track differentiation and progeny in developmental studies of tissues and organisms. The present invention is well-suited for both in vitro and in vivo delivery of desired substances into cells.

In one embodiment, the present invention provides the ability to target transfection to individual neurons within the intact central nervous system using single-cell electroporation. Transfection can be focused to individual cells by confining the extent of exposure to DNA and the applied electric field to the tip of a micropipette. Single-cell electroporation according to the present invention has broad application to different cell types as demonstrated by the transfection of individual optic tectal neurons in the *Xenopus* tadpole brain and pyramidal cells and interneurons in the rat hippocampal slice.

Single-cell electroporation does not appear to have lasting effects on neuronal health. Electroporated neurons expressing GFP had typical morphologies without signs of blebbing or degeneration. Repeated in vivo time-lapse imaging of tadpole neurons demonstrated continuous growth for the entire imaging period, up to 6 days following electroporation. See FIG. 3(a). In addition, the short-term (2 h) dendritic arbor branch dynamics and 24 h growth rates of neurons following single-cell electroporation were similar to those from cells labeled with the lipophillic dye 0.02% 1,1'-dioctadecyl-3,3,3'3'-tetramethylindocarbocyanine perchlorate (DiI, Molecular Probes) (see FIG. 3(c)). This similarity indicates that electroporation, plasmid DNA incorporation, and GFP expression does not interfere with neuronal growth. These findings are supported by a previous study showing that electroporated hippocampal neurons in culture maintain normal synaptic transmission and electrophysiological properties (Teruel, et al., J Neurosci Methods 93, 3748 (1999)).

Although, it is likely that optimal stimulation parameters for single-cell electroporation which transfect cells without causing damage is specific to each cell type and tissue preparation, such parameters may be readily determined by routine experimentation by those skilled in the art. Effective stimulation parameters must balance the requirements for temporary pore formation and DNA electrophoresis against the damaging effects of strong electric fields (Neumann, 1996, supra). Electric field strengths exceeding optimal parameters may result in too many pores or pores too large to reseal, leading to cell lysis. While relatively brief, high voltage pulses are required to disrupt electrostatic forces maintaining the lipid bilayer structure, longer duration, lower amplitude voltage pulses are required for efficient translocation of DNA across the cell membrane (Neumann, 1996, supra). The efficiency of pulses generated by capacitance discharge which have a high initial peak voltage followed by an exponential decay was therefore tested as described below. Indeed, exponential decay pulses yielded high transfection rates. The highest transfection efficiency, however, was elicited by high frequency trains of short duration square pulses.

Using optimized stimulation parameters, high efficiency of co-electroporating individual neurons with two plasmids was accomplished. In the majority of neurons co-transfected with the genes for GFP and DsRed (a fluorochrome protein mutant similar to GFP), both proteins were detected. However, no cells expressing only DsRed were found and any GFP-only cells were relatively dim. It is possible, therefore, that DsRed may have been present in these cells at levels too low to detect with imaging system utilized, due to the fact that the relative brightness of DsRed is 4 times less than GFP (Matz, et al., comments published erratum appears in Nat Biotechnol 1999 December; 17(12):1227. Nat Biotechnol 17, 969–73 (1999)).

Single cell electroporation offers an attractive alternative to other common transfection techniques. One advantage of the present invention is the ease with which multiple genes can be transferred into single cells. When the DNA for different genes is combined and transferred together from the same pipette, the proteins encoded by all the genes are expressed. This feature is a major advance over other electroporation methods such as transferring genes into cells using genetically altered virus, which typically limit the number of genes to one or two. Importantly, electroporation lacks the residual vector agents such as virus, lipofection compounds and gene gun particles which might interfere with neuronal function. In contrast to the apparent long-term health following electroporation, viral infection often leads to cell damage or death within 1 week. Furthermore, the construction of expression vectors such as plasmids for electroporation is relatively routine and inexpensive in contrast to the time and cost required for constructing recombinant viral vectors. Effective electrical stimuli were also produced with relatively inexpensive voltage stimulators common to many neuroscience laboratories.

The ability to target transfection to single cells provides a powerful tool to study gene function in intact nervous systems. The ability to transfer multiple genes into cells is important to studies of the interaction between different proteins. Transferring genes for colored proteins, such as green fluorescent protein, has proven immensely useful for labeling cells in order to visualize their shapes. These dyes can also be attached to other proteins in order to see where these proteins are located and move within the cell. As demonstrated below, single-cell electroporation according to the present invention was used to fill brain cells with protein dyes in order to observe the cells growth within the intact brain over many days. By introducing other genes along with the gene for green fluorescent protein the effects of various proteins on brain cell growth can be observed. Such observations would not be possible if nearby cells also underwent gene transfer and expressed the dyes because it would be impossible to distinguish the unique shapes of individual cells. GFP expression in individual neurons allows imaging of neuronal morphology without interference of fluorescence from neighboring cells. The ability to restrict transfection to single cells ensures that any induced changes are likely due to a cell-autonomous effects of the exogenous genes, and not secondary influences from transfected neighbors.

The following examples are included to illustrate certain aspects of the present invention and are not intended to limit the invention in any manner whatsoever.

EXAMPLE I

Preparation of Organotypic Hippocampal Slices

Organotypic slice culture of hippocampus was prepared as described (Stoppini, et al., J Neurosci Methods 37, 173–82 (1991)). Briefly, hippocampal slices (400 μm) were cut from postnatal 6- to 8-day-old rats with a tissue chopper and incubated on Millicell filters (Millipore) at 37° C., exposed to a combination of 95% $O_2$ and 5% $CO_2$ (Musleh, et al., Proc Natl Acad Sci USA 94, 9451–6 (1997)). Slices were used for single-cell electroporation after 5 to 7 days in culture. Twenty-four to 48 h after transfection, hippocampal slice cultures were fixed in 4% paraformaldehyde in 0.1 M phosphate buffer for 15 min, rinsed with 0.1 M PB, and mounted on glass slides with VectaShield (Molecular Probes, Eugene, Oreg.).

EXAMPLE II

Single-Cell Electroporation

Transfection of single cells was accomplished using electroporation from DNA-filled micropipettes. Micropipettes with a tip diameter of 21 µm, were pulled on a P-87 Micropipette Puller (Sutter Instrument Company, CA), and filled with solution containing plasmid DNA. Plasmid DNA was purified using Promega Wizard Plus MidiPreps DNA purification system (Promega, Madison, Wis.) and resuspended at concentrations ranging from 0.25–2.0 µg/µl in dH$_2$O or 0.1 M phosphate buffer (PB), pH 7.4. A silver wire was placed inside the micropipette in contact with the internal DNA solution. Micropipette holders were mounted on course, 3-axis, manual micromanipulators. Voltage pulses generated by a Grass SD9 Stimulator (Grass-Telefactor, West Warwick, R.I.) were delivered between the micropipette electrode (anode) and a silver wire ground electrode (cathode) placed under the tadpole or brain slice.

For single-cell electroporation in the intact tadpole brain, stage 46–48 tadpoles were anesthetized with 0.02% 3-aminobenzoic acid ethyl ester (MS222, Sigma) in Steinberg's solution (pH 7.4). Anesthetized tadpoles were placed on top of a moistened Kimwipe on the stage of an Olympus BX50 microscope equipped with a 20× long working distance lens. The DNA-containing micropipette was inserted blind into the optic tectum of the tadpole brain in a region with a high density of cell bodies. The resistance of the micropipette electrode ranged from 15 to 30 MΩ in the tadpole brain.

For transfection of single cells in hippocampal slice cultures, a Millicell culture well containing slices was placed in a 35 mm petri dish containing culture medium, on the stage of a dissecting microscope. The micropipette containing DNA was inserted into the stratum pyramidale of areas CA1 or CA3 within the hippocampal slice. Micropipette resistance in the hippocampal slice ranged from 10 to 15 MΩ.

Stimulation parameters for single-cell electroporation including voltage pulse amplitude, duration, and shape were tested for transfection efficiency in the tadpole brain. Transfection efficiency was measured by expression of fluorescence following electroporation with the plasmid pEGFP (Clontech Laboratories, Palo Alto, Calif.), a plasmid carrying the gene for enhanced EGFP driven by a CMV promoter. Two voltage pulse shapes were compared, square pulses and capacitance discharge pulses with a high initial peak followed by an exponential decay. Square pulses were generated with the Grass SD9 stimulator and were delivered as individual stimuli or 1 s trains of 1 ms square pulses. Trains of 1 ms square pulses were delivered at 50 or 200 Hz for 1 sec. To form exponential decay pulses, voltage pulses from the Grass stimulator (200 Hz, 4 ms) were used to charge a capacitor (0.4–3 µF) which was then allowed to discharge across the electrode. The time constant (τ) of decay of the capacitance discharge was controlled by a variable resistor in parallel with the capacitor. Time constants tested ranged from 20 to 70 ms. Voltages for both square and exponential decay pulses were varied between 10 and 70 V, and in each case single stimuli were compared with 5 stimuli delivered at 1 Hz. Limited clogging allowed repeated use of the same micropipette at different sites. Four sites were electroporated in each tadpole. The optimal stimulation parameters for single-cell transfection in the tadpole brain were then tested in the hippocampal slice culture. Tadpoles and brain slices were examined for GFP expression 24 to 48 h after electroporation using a Nikon Optiphot microscope with epifluorescence (20× objective, NA 0.75).

Electroporation of DNA from a micropipette resulted in transfection of single neurons in the *Xenopus* tadpole brain and the cultured rat hippocampal slice (FIGS. 1a–1d). In cells transfected with pEGFP, bright GFP fluorescence in somata, dendrites and axons could be detected within 12 h. In hippocampal pyramidal cells, GFP completely filled all processes including dendritic spines. Fluorescence increased over 2 to 3 days, even with repeated imaging (FIGS. 3a–3c), and remained high for more than 2 weeks.

Figure 2:
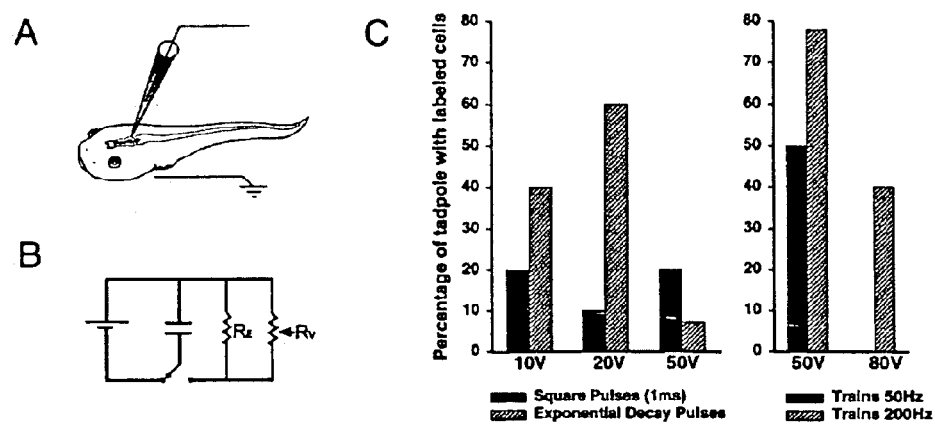
FIG. 2a is a pictorial depiction of single-cell electroporation of a neuron in vivo by insertion of a glass micropipette filled with a DNA solution into the brain of an anesthetized tadpole. Electrical stimulation delivered between the micropipette and an external ground transfects a single cell at the micropipette tip.
FIG. 2b depicts a circuit diagram for delivery of voltage pulses as square pulses or exponential decay pulses. The voltage source is a periodic pulse generator, RE represents the resistance of the electrode in the tadpole, and $R_V$ represents a variable resistor used to control the time constant ($\tau$) of the decay of the exponential pulse. A switch was used to connect the capacitor to the voltage source or to the electrode and variable resistor.
FIG. 2c is a graphical representation which compares the percentage of tadpoles with labeled cells based on the type of voltage pulse. Optimal parameters for single-cell electroporation were dependent on pulse shape and amplitude. All stimuli were delivered 5 times at 1/sec. Exponential decay pulses ($\tau$=70 ms) produced by the circuit depicted in FIG. 2b were more effective than square pulses (1 ms). Highest transfection efficiencies were produced with trains of 1 ms square pulses delivered at 200 Hz.

Single-cell electroporation efficiency tested in the tadpole brain was dependent on stimulation parameters including the number of pulses delivered, voltage amplitude and pulse shape (FIGS. 2b and 2c). Three types of stimuli were tested square pulses, exponential decay pulses produced by capacitance discharge, and high frequency trains of square pulses. Delivery of 5 repeated individual pulses or trains (1 sec in duration) with 1 sec interstimuli intervals were much more effective than individual stimuli, and therefore, 5 repeated pulses or trains were delivered for each parameter tested. Initial tests with 1 ms square pulses at voltages ranging from 10 to 50 V produced low numbers of single cell transfections (FIG. 2c). Transfection efficiency was greatly enhanced by exponential decay pulses with τ=70 ms. Transfection efficiency using exponential decay pulses were voltage dependent with highest rates at a voltage peak of 20 V. Trains of 1 ms square pulses yielded high transfection rates and were frequency and voltage dependent. The highest transfection rates in tadpole brains were with 200 Hz trains of 1 ms square pulses at 50 V. In the rat hippocampal slice culture, trains of 200 Hz stimuli (1 ms pulses) at 20 V were the most effective for transfection of individual neurons, including CA1 and CA3 pyramidal cells (FIGS. 1b–1d), and CA1 interneurons. Transfection efficiency was not noticeably affected by DNA concentration in the range of 0.25 to 2.0 µg/µl, the inclusion of CaCl$_2$ in the DNA solution, or resuspension of DNA in dH$_2$O or phosphate buffer (PB).

EXAMPLE III

Neuronal Growth and Dendritic Branch Dynamics

Time-lapse confocal imaging was used to determine whether single-cell electroporation and subsequent exogenous protein expression interferes with normal neuronal morphology and growth. Both short-term (2 h) dendritic branch dynamics and total dendritic arbor growth over 24 h were compared between neurons transfected with pEGFP by single-cell electroporation and single neurons labeled with DiI (Molecular Probes), a dye commonly used for imaging neuronal morphology (Wu, G. Y. and Cline, H. T., Science 279, 222–6 (1998)). Eleven optic tectal neurons were transfected with pEGFP (0.5 µg/µl) using the optimal stimulation parameters (200 Hz trains, 50 V). Fifteen neurons in the optic tectum were labeled by iontophoresis of DiI dissolved in ethanol, using 3–10 pulses of 200 ms positive current pulses (1–10 nA). Starting 24 h after electroporation, cells were imaged 5 times at 2 h intervals, and then imaged the following day. In addition, some cells were subsequently imaged once-daily for up to 6 days. Dendritic arbors were reconstructed by tracing the portion of the neuron in each acquired optical section onto an acetate sheet until the entire neuron was drawn. Total dendritic branch length was measured from scanned drawings of cells using the program NIH Image 1.61. To analyze the arbor dynamics, drawings of cells from sequential timepoints were superimposed to identify added and retracted branches.

Figure 3:
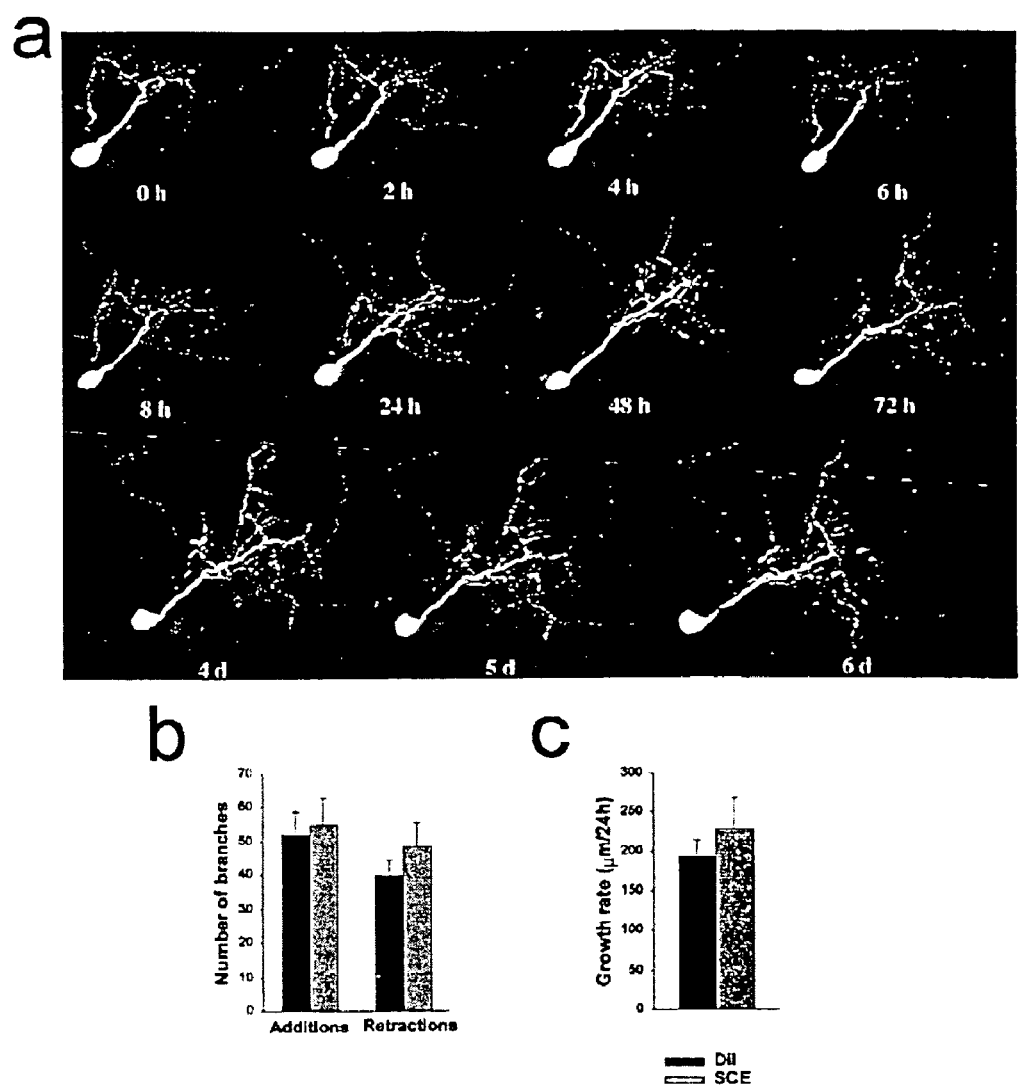
FIG. 3a depicts in vivo time-lapse confocal imaging at 2 h intervals 24 h after electroporation and demonstrates typical rapid axonal and dendritic extensions and retractions. Daily imaging up to 6 days following single-cell electroporation demonstrate that neurons grow continuously and appear healthy.
FIG. 3b is a graphical representation comparing the number of branches, additions and retractions between neurons containing DiI via iontophoresis and neurons containing GFP via single cell electroporation.
FIG. 3c is a graphical representation of growth rate comparing neurons containing DiI via iontophoresis and neurons containing GFP via single cell electroporation. Dendritic growth dynamics at 2 h intervals 24 h after electroporation were similar to the dynamic of tadpole neurons labeled with DiI. The total dendritic arbor growth rates over 24 h of neurons labeled with GFP by single-cell electroporation (SCE) were also similar to neurons labeled with DiI, indicating that electroporation according to the present invention does not adversely affect tectal cell development.

Repeated confocal imaging of neurons in anesthetized tadpoles was utilized to monitor neuronal morphology, dendritic arbor branch dynamics at 2 h intervals, and dendritic arbor growth rates over several days (FIGS. 3a–3c). These parameters were compared in GFP-expressing cells and cells labeled with the DiI. In both DiI-labeled cells and neurons electroporated with GFP, dendritic arbors grew continuously, without signs of dendritic or axonal swelling or degeneration. Dendritic arbor branch additions and retractions measured at 2 h intervals were comparable in the two groups (additions: GFP=55.1±7.6 branches/2 h; DiI= 52.2±6.5 branches/2 h; retractions: GFP=48.6±7.2 branches/2 h; DiI=39.8±4.5 branches/2 h, expressed as mean±SE). Growth rate over 24 h, measured as the total dendritic branch length on day 2 (time after labeling) subtracted by the branch length on day 1, was also similar between groups (GFP=193.7±21.7 $\mu$m/24 h; DiI= 229.5±38.1 $\mu$m/24 h).

EXAMPLE IV

Single Cell Electroporation of Glial Cells

For single-cell electroporation in the rat brain in vivo, rats 14–20 days old were anesthetized with a combination of xylazine (0.03 mg/g body weight) and ketamine (0.56 mg/g body weight), and placed in a stereotaxic apparatus. Body temperature was maintained with a heating pad placed under the rat. A small incision was made in the skin and a small hole (~4 mm) was opened in the skull exposing the brain. A ground electrode was attached to the cut skin using an alligator clip. A micropipette filled with a solution containing plasmid DNA carrying the gene for EGFP (0.5 $\mu$g/$\mu$l) was inserted into the brain tissue at multiple site depths ranging from 100 to 400 $\mu$m. Brief electrical stimuli (1 s trains of 1 ms square pulses at 200 Hz, 20 to 50 V) were delivered between a silver wire within the micropipette and the ground electrode. Following electroporation, the incision was closed and sealed with surgical glue. Two to 4 days following electroporation, rats were euthanized and perfused with phosphate buffered saline (50 ml) followed by 4% paraformaldehyde (50 ml) to fix the brain. Following perfusion, brains were removed and submerged in 4% paraformaldehyde for 12 to 24 hours at 4° C. Brains were then cut into 100 or 200 $\mu$m thick sections with a vibratome which were then mounted on subbed glass slides with VectaShield mounting solution (Molecular Probes) and covered with glass coverslips. Tissue sections were screened for GFP-expressing cells using epifluorescence and transfected cells were imaged with confocal microscopy. Micropipette electroporation in the intact rat brain was shown to have resulted in GFP expression in astrocytes at the site of stimulation.

EXAMPLE V

Electroporation of Multiple Plasmids

In order to determine the efficiency of co-transfecting multiple independent genes, the plasmids pEGFP and pDsRed (Clontech Laboratories) were used together for single-cell electroporation. Fifty neurons in the tadpole optic tectum were transfected using micropipettes containing a mixture of both plasmids (0.5 $\mu$g/$\mu$l of each). Starting 12 h after electroporation and for up to 4 days after, anesthetized tadpoles were examined for GFP and DsRed fluorescence by confocal microscopy.

Figure 4:
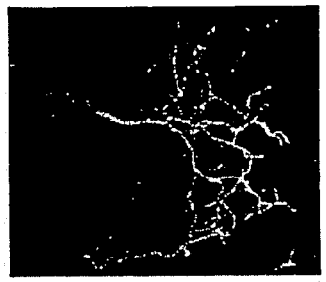
FIG. 4a depicts confocal imaging of a tadpole optic tectal neuron cotransfected with pEGFP and pDsRed using single-cell electroporation with GFP fluorescence excited at 488 nm to emit green.
FIG. 4b depicts confocal imaging of the co-transfected tadpole optic tectal neuron shown in FIG. 4a having DsRed fluorescence when excited at 568 nm to emit red.
FIG. 4c depicts an overlay of confocal imaging of the cotransfected tadpole optical tectal neuron shown in FIGS. 4a and 4b which appears yellow.
Figure 4:
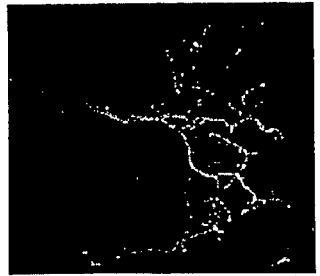
Figure 4:
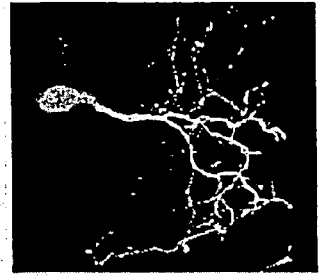
Figure 5:
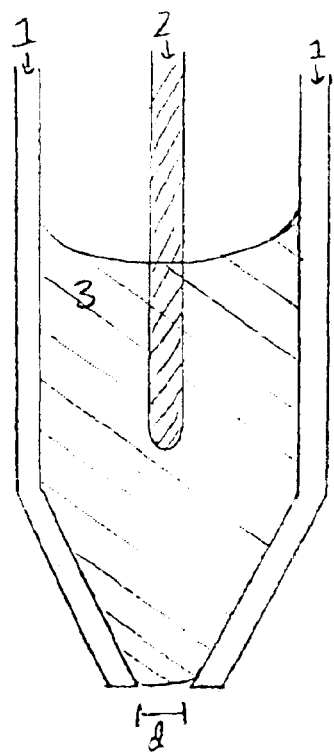
FIG. 5 shows one embodiment of the subject electroporation assembly. 1: pipette wall; 2: wire electrode; 3: delivery solution; 4: ground electrode. Diameter (d) of pipette opening shown here is 0.5 to 1.0 $\mu$m. The two electrodes (2) and (4) connect to a voltage stimulator.
Figure 5:
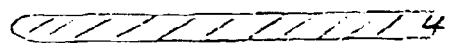
Figures 6A, 6B:
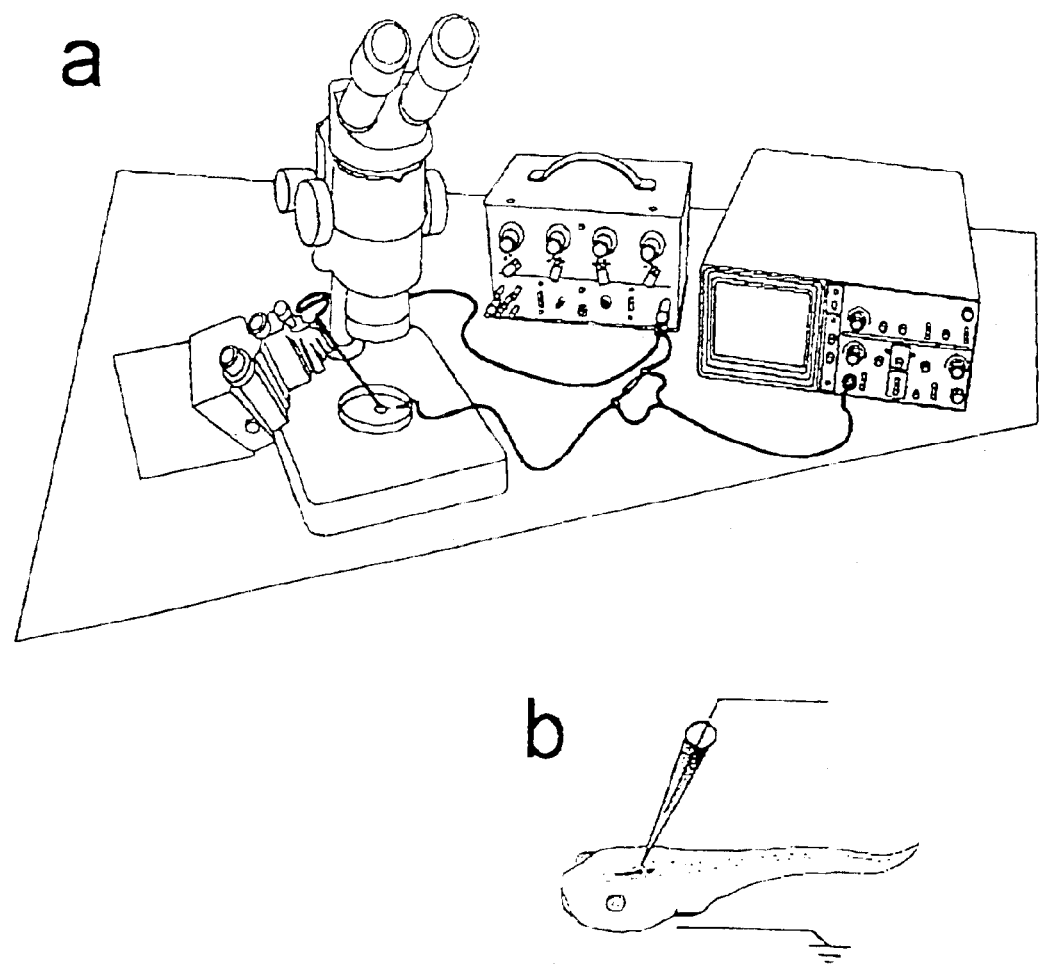
FIG. 6A shows an overall scheme of the electroporation assembly. A pipette having a first electrode disposed therein is shown inserted into a target cell. A second electrode is visible next to the specimen. Both the first and second electrodes are connected to wire leads which in turn are connected to a voltage stimulator. An oscilloscope which measures current, is shown to the right of the voltage stimulator.
FIG. 6B shows a close-up of the electroporation assembly being used for single-cell electroporation into an intact tadpole brain.

Single-cell electroporation with two independent plasmids encoding GFP and DsRed resulted in co-expression of both fluorescent proteins in 92% (46 out of 50) of cells (FIGS. 4a–4c). While GFP fluorescence could be detected within 12 h and steadily increased in intensity over 3 days, detection of DsRed expression was relatively delayed, initially detectable after 24 to 36 h, and increasing over 4 to 5 days. Bright GFP and DsRed fluorescence persisted for more than 2 weeks, the longest time examined. Following co-electroporation, 46 out of 50 cells expressed detectable levels of both GFP and DsRed. The remaining 4 cells exhibited dim GFP with no detectable DsRed. In all cases, GFP was brighter than DsRed and DsRed was never detected without GFP.

EXAMPLE VI

Confocal imaging

GFP and DsRed fluorescence following single-cell electroporation, and DiI labeling was imaged with a confocal microscope comprised of a krypton-argon laser and a Noran XL laser scanning confocal attachment mounted on an upright Nikon Optiphot microscope, using a 40× Nikon oil immersion lens (1.30 NA). Tadpoles were anesthetized with 0.02% MS222 prior to imaging and were allowed to recover between imaging sessions. Hippocampal slice cultures were fixed and mounted on slides before imaging. Images were collected through the entire extent of the neuron at steps of 1 or 2 $\mu$m in the z-dimension. Eight to 16 frames were averaged for each optical section. GFP was excited at 488 nm and emitted light was filtered between 500 nm and 550 nm. DsRed was excited at 568 run and emitted light between 578–632 nm was detected. DiI was excited with 568 nm and emitted light with greater than 590 nm was detected.

It will be understood that various modifications may be made to the embodiments and aspects disclosed herein. For example, it is contemplated that circuits having topology other than that depicted in FIG. 2(b) such as series RC or series RL circuits can be utilized in accordance with the present invention. Therefore, the above description should not be viewed as limiting, but merely as exemplifications of preferred embodiments. Those skilled in the art will envision other modifications within the spirit and scope of the claims appended hereto.

What is claimed is:

1. A method for delivering a substance into a cell said method comprising:
   providing a singular container having a distal opening;
   placing a conductive fluid including a substance in the container;
   placing the distal opening in proximity to the cell without penetrating a cell membrane; and
   causing an electrical signal to pass through the conductive fluid and the cell, said electrical signal having changeable voltage parameters, wherein electrical signal opens pores in the cell and the substance passes through the distal opening and enters the cell through the pores.

2. A method for delivering a substance into a cell according to claim 1 wherein the container is selected from the group consisting of pipette, buret and syringe.

3. A method for delivering a substance into a cell according to claim 2 wherein the pipette is a micropipette.

4. A method for delivering a substance into a cell according to claim 3 wherein the micropipette is a glass pulled pipette having a sharp tip opening having a diameter less than the diameter of the cell.

5. A method for delivering a substance into a cell according to claim 1 wherein the electrical signal passes between first and second electrodes, the first electrode having at least a portion thereof disposed within the container and in direct electrical communication with the conductive fluid.

6. A method for delivering a substance into a cell according to claim 1 wherein the cell is in direct contact with the distal opening.

7. A method for delivering a substance into a cell according to claim 1 wherein the substance is selected from the group consisting of nucleic acid, dye, protein, antibody, antigen, peptide, metal, pharmaceutical compound, a radio-labeled derivative of the foregoing and combinations thereof.

8. A method for delivering a substance into a cell according to claim 7 wherein the nucleic acid is contained in a vector.

9. A method for delivering a substance into a cell according to claim 7 wherein the dye is a fluorochrome.

10. A method for delivering a substance into a cell according to claim 7 wherein the protein is a fluorochrome.

11. A method for delivering a substance into a cell according to claim 10 wherein the protein is green fluorescent protein or a red shifted mutant thereof.

12. A method for delivering a substance into a cell according to claim 7 wherein the nucleic acid is a nucleic acid encoding a fluorescent protein.

13. A method for delivering a substance into a cell according to claim 12 wherein the fluorescent protein is green fluorescent protein or a color shifted mutant thereof.

14. A method for delivering a substance into a cell according to claim 1 wherein the electrical signal is generated by a periodic pulse generator.

15. A method for delivering a substance into a cell according to claim 14 wherein the electrical signal is a square pulse.

16. A method for delivering a substance into a cell according to claim 15 wherein the electrical signal is a high frequency train of square pulses.

17. A method for delivering a substance into a cell according to claim 14 wherein the electrical signal is an exponential decay pulse.

18. A method for delivering a substance into a cell according to claim 1 wherein the cell is a neuron.

19. A method for delivering a substance into a cell according to claim 1 wherein the cell is a brain cell selected from the group consisting of neuron and glial cell.

20. A method for delivering a substance into a cell according to claim 1 wherein the method is conducted in vivo.

21. A method for delivering a substance into a cell according to claim 1 wherein the method is conducted in vitro.

* * * * *